United States Patent
Schousboe et al.

(10) Patent No.: US 11,781,980 B2
(45) Date of Patent: Oct. 10, 2023

(54) FETAL LUNG MATURITY TEST

(71) Applicant: SIME DIAGNOSTICS LTD., London (GB)

(72) Inventors: Peter Schousboe, Odense (DK); Henrik Verder, Bagsværd (DK)

(73) Assignee: Sime Diagnostics Ltd., London (GB)

(*) Notice: Subject to any disclaimer, the term of this patent is extended or adjusted under 35 U.S.C. 154(b) by 537 days.

(21) Appl. No.: 16/754,009

(22) PCT Filed: Oct. 5, 2018

(86) PCT No.: PCT/EP2018/077090
§ 371 (c)(1),
(2) Date: Apr. 6, 2020

(87) PCT Pub. No.: WO2019/068848
PCT Pub. Date: Apr. 11, 2019

(65) Prior Publication Data
US 2020/0400558 A1    Dec. 24, 2020

(30) Foreign Application Priority Data
Oct. 6, 2017  (EP) ..................... 17195178

(51) Int. Cl.
*G01N 33/92*  (2006.01)
*G01N 21/3577*  (2014.01)
*G01N 1/40*  (2006.01)
*G01N 33/487*  (2006.01)

(52) U.S. Cl.
CPC ....... *G01N 21/3577* (2013.01); *G01N 1/4077* (2013.01); *G01N 33/487* (2013.01); *G01N 33/92* (2013.01); *G01N 2001/4083* (2013.01); *G01N 2405/04* (2013.01); *G01N 2405/08* (2013.01); *G01N 2800/12* (2013.01)

(58) Field of Classification Search
CPC ............. G01N 21/3577; G01N 1/4077; G01N 33/487; G01N 33/92; G01N 2001/4083; G01N 2405/04; G01N 2405/08; G01N 2800/12; G01N 2021/3595; A61B 5/08; A61B 5/4362; A61B 2503/045
USPC ................................. 600/310, 313; 514/789
See application file for complete search history.

(56) References Cited

U.S. PATENT DOCUMENTS

2016/0103143 A1* 4/2016 Verder .................. G01N 21/35
702/21

FOREIGN PATENT DOCUMENTS

| WO | 92/19232 | 11/1992 |
| WO | 2014/191406 | 12/2014 |

OTHER PUBLICATIONS

Beintema-Dubbeldam, et al ("Determination of Lamellar Body Phospholipids in Amniotic Fluid: A Method to Predict when the Fetal Lung Becomes Mature" Gynecol. Obstet. Invest. 21: 64-69 (1986) (Year: 1986).*
Verder, et al ("Rapid test for lung maturity, based on spectroscopy of gastric aspirate, predicted respiratory distress syndrome with high sensitivity," Acta Paediatrica 2017, 106, pp. 430-437 (Year: 2017).*

(Continued)

*Primary Examiner* — Michael Maskell
(74) *Attorney, Agent, or Firm* — Dinsmore & Shohl LLP; Weston R. Gould

(57) ABSTRACT

The present invention relates to methods for diagnosing Respiratory Distress Syndrome of newborn.

17 Claims, 3 Drawing Sheets

(56) References Cited

OTHER PUBLICATIONS

Verder, H. et al., "Early surfactant guided by lamellar body counts on gastric aspirate in very preterm infants", Neonatology, vol. 104, No. 2, p. 116-122, Jul. 9, 2013.
Verder, H. et al., "Lamellar body counts on gastric aspirates for prediction of respiratory distress syndrome", ACTA Paediatrica, vol. 100, No. 2, Oct. 4, 2010, p. 175-180.
Verder, H. et al., "Prediction of respiratory distress syndrome by the microbubble stability test on gastric aspirates in newborns of less than 32 weeks' gestation", Acta Pædiatr. 92, p. 728-733, 2003, Taylor & Francis, ISSN 0803-5253.
Verder, H. et al., "Rapid test for lung maturity, based on spectroscopy of gastric aspirate, predicted respiratory distress syndrome with high sensitivity" ACTA Paediatrica, vol. 106, No. 3, Dec. 20, 2016, p. 430-437.
Liu , K.et al., "Comparison of infrared spectroscopic and fluorescence depolarization assays for fetal lung maturity", American Journal of Obstetrics and Gynecology, vol. 183, No. 1, Jul. 1, 2000, p. 181-187.
Liu, K. et al.; "Rapid determination of fetal lung maturity from infrared spectra of amniotic fluid", Natioanl, Research Council of Canada publ. No. 34786, Am. J. Obstet Gynecol, vol. 178, No. 2, Feb. 1998.
Peneff, P. et al., "Determination of lecithin and aphingomyelin (L/S ratio) in gastric and/or pharyngeal aspirates of the newborn", Minerva Pediat, Torino, IT, vol. 31, No. 11, Jun. 15, 1979, p. 835-840.
Barr, P. et al., "Lecithin/sphingomyelin ratio in hypopharyngeal aspirate of newborn infants", Archives of Disease in Childhood, vol. 50, Jan. 1, 1975, p. 856-861.
Bevilacqua G., "Prophylaxis of respiratory distress syndrome by treatment with modified porcine surfactant at birth: a multicentre prospective randomized trial", J. Perinat Med., 1996; 24(6): 609-20.
Wendell Jones et al; "Enzymatic Measurement of hosphatidyiglycerol in Aminotic Fluid"; Clin. Chem; Jan. 1, 1992.
English translation of abstract—H. Verder Doctorial dissertation.
Henrik Verder et al.: "Nasal Continous Positive Airway Pressure and Early Surfactant Therapy for Respiratory Distress Syndrome in Newborns of Less Than 30 Weeks' Gestation", Pediatrics vol. 103, No. 2 Feb. 1999.
Henrik Verder, "Nasal CPAP has become an indispensable part of the primary treatment of newborns with respiratory distress syndrome", Acta Pædiatrica 96 ISSN 0803-5253, 2007, p. 482-484.
J. Kamper et al., "Early treatment with nasal continous positive airway pressure in very low-birth-weight infants" Acta Pædiatr 82: 193-7, 1993.
Polin RA and Shani R., "Newer experiance with CPAP", Semin Neonatol, Oct. 7, 2002; (5)., 379-89.
Sandri F. et al.: "Prophylactic or Early Selective Surfactant Combined With nCPAP in Very Preterm Infants", Pediatrics vol. 125, No. 6, Jun. 2010.
Soll R., "Early versus delayed selective surfactant treatment for neonatal respiratory distress syndrome (Review)" The Cochrane Library, 1999, Issue 4.
Soll RF., "Prophylactic versus Selective Use of Surfactant in Preventing Morbidity and Mortality in Preterm Infants", Cochrane Review Upodate, Neonatology 2012; 102:169-171.
Stevens T.P."Early surfactant administration with brief ventilation vs. selective surfactant and continued mechanical ventilation for preterm infants with or at risk for respiratory distress syndrome", Cochrane Database Syst. Rev., Oct. 17, 2007;(4).
van Kaam AH et al.: "Surfactant replacement therapy in preterm infants: a European Survey", Neonatology, 2011; 100(1):71-7.
Verder H. et al., "Surfactant Therapy and Nasal Continuous Positive Airway Pressure for Newborns with Respiratory Distress Syndrome", New England Journal of Medicine, 331, 1051-1055 Oct. 20, 1994.
Verder H., Frontpage of Disputate: "Prænatal bestemmelse af lungematuriteten og forebyggelse af idiopatisk respiratory distress syndrom. Lecithinsphingomyelin ration i amnionvæsken", Doctorial dissertation Nov. 27, 1980 at University of Copenhagen.
Anonymous: "Lamellar granule—Wikipedia"; Mar. 13, 2017.
Beintema-Dubbledam et al; "Determination of lamellar body phospholipids in amniotic fluid a method to predict when the fetal lung becomes mature"; Gynecologic and Bostetric Investigation, vol. 21, No. 2, 1986, pp. 64-69.
Besnard et al; "Lecithin/sphingomyelin ratio and lamellar body count for fetal lung maturity: a meta-analysis"; European Journal of Bostetrics 6 Gynecology and Reproductive Biology; vol. 169, No. 2, Jul. 1, 2013, pp. 177-183.
Piazze et al; "Lamellar bodies:platelet channel particles as predictors of respiratory distress syndrome (RDS) and of transient tachypnea of the newborn", Journal of Perinatal Medicine, vol. 39, No. 3, May 2011, pp. 349-351.
Wang et al; "Proteomic analysis of lamellar bodies isolated from rat lungs"; BMC Cell Biology, Biomed Central, London, GB, vol. 9, No. 1, Jun. 24, 2008, p. 34.
Chinese Journal of Pediatrics, 1995, vol. 33, No. 4 p. 226-228 and English translation of abstract.

\* cited by examiner

FETAL LUNG MATURITY TEST

CROSS REFERENCE TO RELATED APPLICATIONS

This application is a U.S. National Stage of international application PCT/EP2018/077090 filed Oct. 5, 2018, which claims priority to European Application No: 17195178.3 filed Oct. 6, 2017, the entire contents of each of which are incorporated herein by reference.

TECHNICAL FIELD

The present invention relates to methods for diagnosing Respiratory Distress Syndrome of newborns.

BACKGROUND

Surfactant deficiency at birth and development of Respiratory Distress Syndrome of newborn (RDS) is the most important cause of morbidity and mortality in preterm infants.

Respiratory Distress Syndrome

Respiratory Distress Syndrome (RDS) also called idiopathic respiratory distress syndrome (IRDS) or neonatal respiratory distress syndrome [1], and hyaline membrane disease (HMD), is a syndrome in premature infants caused by developmental insufficiency of surfactant production and structural immaturity in the lungs. It can also be the result of genetic causes, challenging production of surfactant associated proteins. RDS affects about 1% of newborn infants and is the single leading cause of death and morbidity in preterm infants [2]. The incidence decreases with advancing gestational age, from about 50% in babies born at 26-28 weeks, to about 25% at 30-31 weeks. The syndrome is more frequent in infants of diabetic mothers, in the second born of premature twins, and in infants born under induced labours or caesarean sections.

The onset of RDS is shortly after birth, and is manifested by tachypnea, tachycardia, chest wall retractions (recession), expiratory grunting, nasal flaring and cyanosis during breathing efforts. As the disease progresses, the newborn may develop ventilatory failure (rising carbon dioxide concentrations in the blood), and prolonged cessations of breathing ("apnea"). Whether treated or not, the clinical course for the acute disease lasts for about 2 to 5 days. During the first days the condition of the patient often worsens and requires more support. Despite major advances in care, RDS remains the most common single cause of death in the first month of life. Complications include metabolic disorders (acidosis, low blood sugar), patent ductus arteriosus, low blood pressure, chronic lung changes, and intracranial haemorrhage. The disease is frequently complicated by prematurity and its accompanying defects in other organ functions.

The characteristic histopathology seen in babies who die from RDS was the source of the name "hyaline membrane disease". Waxy-appearing layers of hyaline membrane line the collapsed alveoli of the lung. In addition, the lungs show bleeding, over-distention of airways and damage to the lining cells.

Moderate to severe cases of RDS will progress if the condition is not treated. Early nasal continuous positive airway pressure (nCPAP) decreases or halts the progression so that mechanical ventilation (MV) can be avoided in many cases [3-5].

In addition, about half of infants with RDS treated with nCPAP need surfactant supplementation to stop the progression [6,7] as the lungs of infants with RDS are developmentally deficient of surfactant. Similarly, about 50% of infants treated with MV need surfactant [8]. These infants, in contrast to infants treated with nCPAP, often require more doses of surfactant for a sustained response [6].

Surfactant

Surfactant is a surface-active lipoprotein complex produced by specialized lung cells called Type II cells or Type II pneumocytes. The proteins and lipids that comprise the surfactant have both a hydrophilic region and a hydrophobic region. By adsorbing to the air-water interface of alveoli with the hydrophilic head groups in the water and the hydrophobic tails facing towards the air, the main lipid component of surfactant, dipalmitoylphosphatidylcholine (DPPC), reduces surface tension. In addition to DPPC which constitutes about 40%, the surfactant complex comprises about 40% other phospholipids, about 5% surfactant-associated proteins (SP-A, B, C and D) and additionally cholesterol and trace amounts of other substances.

The function of the surfactant complex is to increase pulmonary compliance, to prevent atelectasis (collapse of the lung) at the end of expiration and to facilitate recruitment of collapsed airways.

Surfactant helps prevent collapse of the terminal airspaces throughout the normal cycle of inhalation and exhalation. The surfactant is packaged by the cell in structures called lamellar bodies, and extruded into the air-spaces. The lamellar bodies subsequently unfold into a complex lining of the air-space. This layer reduces the surface tension of the fluid that lines the air-space. Surface tension is responsible for approximately ⅔ of the elastic recoil forces. In the same way that a bubble will contract to give the smallest surface area for a given volume, at the air/water interface the liquid surface will tend towards being as small as possible, thereby causing the air-space to contract. By reducing surface tension, surfactant prevents the air-spaces from completely collapsing on exhalation. In addition, the decreased surface tension allows re-opening of the air-space with a lower amount of force. Therefore, without adequate amounts of surfactant, the air-spaces collapse and are very difficult to expand. Microscopically, a surfactant deficient lung is characterized by collapsed air-spaces alternating with hyperexpanded areas, vascular congestion and, in time, hyaline membranes. Hyaline membranes are composed of fibrin, cellular debris, red blood cells, rare neutrophils and macrophages. They appear as an eosinophilic, amorphous material, lining or filling the air spaces and blocking gas exchange. As a result, blood passing through the lungs is unable to pick up oxygen and unload carbon dioxide. Blood oxygen levels fall and carbon dioxide rises, resulting in rising blood acid levels and hypoxia. Structural immaturity, as manifest by decreased number of gas-exchange units and thicker walls, also contributes to the disease process. Therapeutic oxygen and positive-pressure ventilation, while potentially life-saving, can also damage the lung. The current diagnosis is based on the clinical condition supplemented by chest x-ray, which demonstrates decreased lung volumes (bell-shaped chest), a small (0.5-1 mm), discrete, uniform infiltrate (sometimes described as a "ground glass" appearance) that involves all lobes of the lung, and air-bronchograms (i.e. the infiltrate will outline the larger airways passages which remain air-filled). In severe cases, this becomes exaggerated until the cardiac borders become unapparent (a 'white-out' appearance).

In pregnancies of greater than 30 weeks, the fetal lung maturity may be tested by sampling the amount of surfactant in the amniotic fluid by amniocentesis, wherein a sampling syringe needle is inserted through the mother's abdomen and uterus. Several tests are currently available that correlate the production of surfactant. One of the most important tests involves measurement of the concentration ratio between the phospholipids lecithin and sphingomyelin, the so called "L/S ratio". An L/S ratio of less than about 2.0 was previously found to be an indication that the fetal lungs are deficient [9].

A therapeutic standard procedure in very preterm infants has been to start with nCPAP, and, as surfactant is better administered early than late [6,10,11], to give surfactant during a short intubation as soon as clinical symptoms and an increasing oxygen requirement indicate moderate to severe RDS [6,12]. This so-called INSURE (intubation surfactant extubation) procedure is now widely used and has resulted in diminished use of MV [10] and a decreased incidence of bronchopulmonary dysplasia (BPD) [11,13]. Many infants are still given surfactant relatively late—typically the median age at treatment is 5 h [4]. Additionally, common clinical criteria for identification of infants with RDS in need of surfactant and timing of this treatment are missing [14]. Consequently, there is a need for a rapid quantitative method to identify which of the very preterm infants who are at risk of failing nCPAP and who therefore should receive surfactant at an early stage. Prophylactic surfactant treatment as an alternative has proven suboptimal [13]. Preferably the diagnosis and treatment should start immediately after birth. The present state of the art methods requires time-consuming laboratory tests to be performed thus delaying diagnosis and onset of medication for those in need thereof [15].

Lamellar Bodies

Lamellar bodies are also termed lamellar granules, membrane-coating granules (MCGs), keratinosomes or Odland bodies. They are lipid storage and secretory organelles found in type II alveolar cells in the lungs, and in keratinocytes in the skin. They are oblong structures, appearing about 300-400 nm in length and 100-150 nm in width in transmission electron microscopy images. Lamellar bodies fuse with the cell membrane and release pulmonary surfactant into the extracellular space. They are surrounded by a membrane and contain multilamellar lipid membranes. They may also contain apolipoproteins and lytic enzymes and have an acidic pH. Under normal physiological conditions, their main function is the supply of extracellular domains with specialised lipid components related to a specialised function. The lamellar bodies of the lung epithelium are the storage form of lung surfactant. They provide a monomolecular lipid film of dipalmitoyl phosphatidylcholine on the surface of alveoli to lower surface tension necessary for optimal gas exchange. They also provide a hydrophobic protective lining against environmental influences. Lamellar bodies are also found in other cell types of the respiratory system, for example the mucosa of the nose and the bronchia.

The gastrointestinal tract, the tongue papillae, the oral epithelium and mucosal cells of the stomach also contain lamellar bodies. Phosphatidylcholine is the major phospholipid of lamellar bodies in mucosa cells of the stomach, providing a hydrophobic protective lipid film against the tissue-damaging activities of gastric juice.

The hydrophobic water-protective barrier of the skin also originates from lamellar bodies secreted by epithelial cells, and consists mainly of neutral lipids. Lamellar bodies also occur in mesodermal cell layers of sliding surfaces to provide joint lubrication, as well as in the peritoneum, the pericardium and the pleural mesothelium.

Lamellar bodies have also been found to accumulate in several pathological conditions, such as atherosclerosis, Niemann-Pick disease. The fact that lysosomal lamellar bodies are absent in the normal intima of the aortic wall, but appear in cells in fatty streaks might indicate that their formation is relevant to the pathogenetic mechanisms which become involved in the development of atherosclerosis.

SUMMARY

Figure 1:
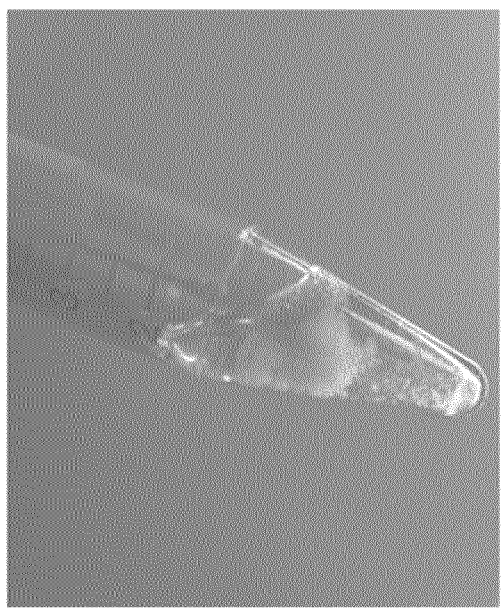
FIG. 1 Left panel: frozen and thawed gastric aspirate samples show mucus-like, flocculent material, mainly composed of phospholipids and proteins. Right panel: fresh gastric aspirate samples do not show flocculent material.
Figure 1:
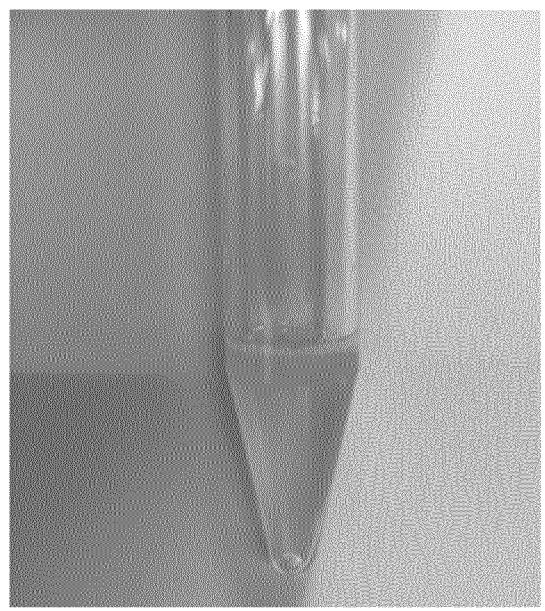

The invention is as defined in the claims.

Herein is provided a method for diagnosing Respiratory Distress Syndrome (RDS), the method comprising the steps of:
i) centrifuging a sample obtained from a subject to obtain a pellet comprising lamellar bodies, and a supernatant;
ii) discarding the supernatant and resuspending the pellet, thereby obtaining a sample for analysis;
iii) analysing the sample to determine a concentration of lecithin or saturated lecithin and optionally an L/S ratio and predict if the subject suffers from Respiratory Distress Syndrome (RDS).

Also provided is a method of treatment of Respiratory Distress Syndrome (RDS) in a newborn individual, comprising the steps of:
i) analysing a sample obtained from a subject to determine a concentration of lecithin or saturated lecithin and optionally an L/S ratio and determining if the subject suffers from RDS as described herein;
ii) if the subject suffers from RDS, administering a therapeutically effective amount of surfactant to the newborn individual.

Also provided is a computer implemented method for diagnosing RDS based on spectral data acquired from a sample obtained from a subject, the method comprising the steps of:
i) acquiring data from the sample to determine the concentration of lecithin or saturated lecithin and optionally the L/S ratio;
ii) correlating said concentration with a control concentration and optionally said ratio with a control ratio, wherein a concentration differing from the control concentration or a ratio differing from the control ratio is indicative of RDS of the subject.

Also provided is a computer program product having a computer readable medium, said computer program product suitable for diagnosing RDS of a subject based on spectral data acquired from a sample obtained from said subject, said computer program product comprising means for carrying out all the steps of the diagnostic methods disclosed herein.

Also provided is a system for diagnosing RDS based on a sample obtained from said subject, comprising
means for measuring spectral data from said sample,
processing means configured for
  a) determining the concentration of lecithin or saturated lecithin and/or determining the L/S ratio, and
  b) correlating said concentration with a control value and/or said ratio with a control ratio, and
  c) indicating whether the concentration differs from the control value and/or whether the ratio differs from the control ratio, wherein a predefined difference is indicative of Respiratory Distress Syndrome (RDS) of the subject.

Herein is provided a method for diagnosing Respiratory Distress Syndrome (RDS), the method comprising the steps of:
  iv) centrifuging a sample obtained from a subject to obtain a pellet comprising lamellar bodies, and a supernatant;
  v) discarding the supernatant and resuspending the pellet, thereby obtaining a sample for analysis;
  vi) analysing the sample to determine the L/S ratio and predict if the subject suffers from Respiratory Distress Syndrome (RDS).

Also provided is a method of treatment of Respiratory Distress Syndrome (RDS) in a newborn individual, comprising the steps of:
  iii) analysing a sample obtained from a subject to determine an L/S ratio and determining if the subject suffers from RDS as described herein;
  iv) if the subject suffers from RDS, administering a therapeutically effective amount of surfactant to the newborn individual.

Also provided is a computer implemented method for diagnosing RDS based on spectral data acquired from a sample obtained from a subject, the method comprising the steps of:
  iii) acquiring data from the sample to determine the L/S ratio;
  iv) correlating said ratio with a control ratio, wherein a ratio differing from the control ratio is indicative of RDS of the subject.

Also provided is a computer program product having a computer readable medium, said computer program product suitable for diagnosing RDS of a subject based on spectral data acquired from a sample obtained from said subject, said computer program product comprising means for carrying out all the steps of the diagnostic methods disclosed herein.

Also provided is a computer implemented method for diagnosing RDS based on spectral data acquired from a sample obtained from a subject, the method comprising the steps of:
  i) determining the L/S ratio in the sample,
  ii) correlating said ratio with a control ratio, wherein a ratio differing from the control ratio is indicative of RDS of the subject.

Also provided is a system for diagnosing RDS based on a sample obtained from said subject, comprising
means for measuring spectral data from said sample,
processing means configured for
  a) determining the L/S ratio, and
  b) correlating said ratio with a control ratio, and
  c) indicating whether the ratio is differing from the control ratio, wherein a predefined difference is indicative of Respiratory Distress Syndrome (RDS) of the subject.

DETAILED DESCRIPTION

Definitions

Analysis Means

The term 'analysis means' as used herein refers to an instrument capable of detecting the physical property of a molecule or group of molecules. In one embodiment the analysis means is a FTIR spectrometer. Preferably the analysis means is an FTIR spectrometer capable of performing measurements in very small sample volumes such as down to 1 µL.

Mid-IR

The term Mid-IR or Mid wavelength infrared, also called intermediate infrared (IIR) and mid-red FTIR spectroscopy as used herein refers to light having a wavelength of between about 3 to about 50 µm.

Premature Infant

The term premature infant as used herein refers to an infant born before or up to 37 weeks into the pregnancy.

Respiratory Distress Syndrome of Newborn

The term "Respiratory Distress Syndrome" (RDS) as used herein refers to the term as understood by those of skill in the art. RDS may also be defined as P22.0 of WHO's ICD-10 disease classification. The abbreviation RDS stands for Respiratory Distress Syndrome.

Method of Diagnosing RDS

It is essential for the success of treatment of respiratory distress syndrome (RDS) in newborn premature infants, to rapidly assess the status of the development of the lungs of the infant. This can be performed by measuring the amount of lecithin and sphingomyelin. However, the methods known to date require sample preparation which is time consuming and thus delays commencement of medication by surfactant. The methods of the current state of the art furthermore typically rely on samples which can be heterogeneous, thus affecting the reproducibility—and consequently the reliability of the diagnosis. Moreover, since the samples are derived from newborns, it is important that the volume required for analysis is as small as possible, which is a challenge for conventional methods.

The present inventors have found that measuring the amount of lecithin and optionally of sphingomyelin in the lamellar bodies contained in a sample obtained from the newborn can be used to reliably predict RDS. The methods are fast and require but minute sample volumes and provide reliable and reproducible results.

The present inventors have thus addressed the above problems and found that it is possible to analyse very low volume samples from e.g. gastric aspirate samples obtained from the newborn individual and to determine the concentration of lecithin or saturated lecithin and optionally the ratio between lecithin and sphingomyelin in the lamellar bodies contained in the samples, without time-consuming laboratory sample preparations.

The present methods are thus based on precipitating said lamellar bodies, removing at least part of the cellular debris from the samples, and determining the concentration of lecithin or saturated lecithin and or the L/S ratio with analysis means. The inventors have surprisingly found that the L/S ratio as determined by the present methods can reproducibly and reliably be used to diagnose RDS in such a short time frame that the methods are well suited for point of care units.

Thus in a main aspect the present invention concerns a method for diagnosing Respiratory Distress Syndrome (RDS), the method comprising the steps of:
i) providing a sample from said subject, wherein the sample is an amniotic fluid sample, a blood sample, an oropharyngeal secretion or a gastric aspirate sample;
ii) diluting and/or homogenising said sample in a first volume of a first solution, thereby obtaining a homogenous sample;
iii) centrifuging the sample of step ii) to obtain a pellet comprising lamellar bodies, and a supernatant;
iv) discarding the supernatant and resuspending the pellet in a second volume of a second solution, thereby obtaining a sample for analysis;
v) determining the amount of a first compound selected from lecithin and saturated lecithin and optionally the amount of sphingomyelin in the sample for analysis, using analysis means;
vi) obtaining a concentration of the first compound and/or a ratio between the first compound and sphingomyelin;
vii) correlating the concentration of vi) with a control value, wherein a concentration equal to or lower than the control value is indicative of the subject having Respiratory Distress Syndrome (RDS); and/or correlating the ratio of vi) with a control ratio, wherein a ratio equal to or lower than the control ratio is indicative of the subject having Respiratory Distress Syndrome (RDS).

In a further aspect, a method of treatment of Respiratory Distress Syndrome (RDS) in a newborn individual is provided, comprising the steps of:
i) providing a sample such as an amniotic fluid sample, a blood sample, an oropharyngeal secretion or a gastric aspirate sample from said newborn individual;
ii) diluting and homogenising said sample in a first volume of a first solution, thereby obtaining a homogenous sample;
iii) centrifuging the homogenous sample to obtain a pellet comprising lamellar bodies and a supernatant;
iv) discarding the supernatant and resuspending the pellet in a second volume of a second solution, thereby obtaining a sample for analysis;
v) determining the amount of a first compound selected from lecithin and saturated lecithin and optionally the amount of sphingomyelin in the sample for analysis, using analysis means;
vi) obtaining a concentration of the first compound and optionally a ratio between the first compound and sphingomyelin;
vii) correlating the concentration of vi) with a control value and optionally the ratio of vi) with a control ratio, wherein a concentration equal to or less than the control value and/or a ratio equal to or less than the control ratio is indicative of Respiratory Distress Syndrome (RDS) of the subject;
viii) if the concentration of vi) is equal to or less than the control value and/or if the ratio of vi) is equal to or less than the control ratio, administering a therapeutically effective amount of surfactant to the newborn individual.

Thus in one aspect the present invention concerns a method for diagnosing Respiratory Distress Syndrome (RDS), the method comprising the steps of:
i) providing a sample from said subject, wherein the sample is an amniotic fluid sample, an oropharyngeal secretion or a gastric aspirate sample;
ii) diluting and/or homogenising said sample in a first volume of a first solution, thereby obtaining a homogenous sample;
iii) centrifuging the sample of step ii) to obtain a pellet comprising lamellar bodies, and a supernatant;
iv) discarding the supernatant and resuspending the pellet in a second volume of a second solution, thereby obtaining a sample for analysis;
v) determining the amount of a first compound selected from lecithin and saturated lecithin and the amount of sphingomyelin in the sample for analysis, using analysis means;
vi) obtaining a ratio between the first compound and sphingomyelin;
vii) correlating the ratio of vi) with a control ratio, wherein a ratio differing from the control ratio is indicative of the subject having Respiratory Distress Syndrome (RDS).

In a further aspect, a method of treatment of Respiratory Distress Syndrome (RDS) in a newborn individual is provided, comprising the steps of:
i) providing a gastric aspirate sample from said newborn individual;
ii) diluting and homogenising said sample in a first volume of a first solution, thereby obtaining a homogenous sample;
iii) centrifuging the homogenous sample to obtain a pellet comprising lamellar bodies and a supernatant;
iv) discarding the supernatant and resuspending the pellet in a second volume of a second solution, thereby obtaining a sample for analysis;
v) determining the amount of a first compound selected from lecithin and saturated lecithin and the amount of sphingomyelin in the sample for analysis, using analysis means;
vi) obtaining a ratio between the first compound and sphingomyelin;
vii) correlating the ratio of vi) with a control ratio, wherein a ratio differing from the control ratio is indicative of Respiratory Distress Syndrome (RDS) of the subject;
viii) if the ratio of vi) is less than the control ratio, administering a therapeutically effective amount of surfactant to the newborn individual.

In a clinical setting, the physician utilising the present methods may, based on the result of the diagnostic method, apply the method of exclusion to determine if the subject wherefrom the sample has been obtained, is suffering from RDS. If the result of the method indicates a concentration of lecithin or saturated lecithin equal to or less than 49.0 µmol/L, or if the result of the method indicates an L/S ratio significantly above a control ratio, the subject does not suffer from RDS. If the clinician determines that the condition of the subject is severe, but that the concentration of lecithin or the L/S ratio is significantly above a control ratio, the clinician can thus conclude that the subject is suffering from a critical condition other than RDS, and continue analysis and apply the appropriate treatment.

Samples

The present methods may be performed on a sample selected from an amniotic fluid sample, a blood sample, an oropharyngeal secretion sample or a gastric aspirate sample. In one embodiment, the sample is an amniotic fluid sample. In another embodiment, the sample is an oropharyngeal secretion sample. In another embodiment, the sample is a gastric aspirate sample. In another embodiment, the sample is a blood sample.

If the sample is obtained from amniotic fluid, care should be taken to prevent contamination of the amniotic fluid. In one embodiment, the sample is obtained from a subject, such as a human being e.g. a female, such as a pregnant female.

The chances of collecting non-contaminated or essentially non-contaminated amniotic fluid are good in connection with caesarean sectioning. Thus in one embodiment the subject is a female human being, undergoing, or immediately about to undergo, caesarean sectioning. In a further embodiment the body fluid sample is amniotic fluid collected from the female human being, during or immediately subsequent to the caesarean sectioning.

As mentioned above, the present method allows for very small sample volumes. In one embodiment, the sample has a volume between 10 and 1000 µL, such as between 10 and 750 µL, such as between 20 and 500 µL, such as between 30 and 250 µL, such as between 40 and 125 µL, such as between 50 and 100 µL, such as between 60 and 90 µL, such as between 70 and 80 µL, such as 50 µL, 75 µL or 100 µL. In some embodiments, the sample has a volume less than 1000 µL, such as less than 900 µL, such as less than 800 µL, such as less than 700 µL, such as less than 600 µL, such as less than 500 µL, such as less than 400 µL, such as less than 300 µL, such as less than 200 µL, such as less than 100 µL, such as less than 90 µL, such as less than 80 µL, such as less than 70 µL, such as less than 60 µL, such as less than 50 µL. In specific embodiments, the volume of the sample is 50 µL, 75 µL or 100 µL.

Preferably, the sample is untreated prior to performing the present methods. Care should be taken however to try and obtain a sample which is as homogeneous as possible. Step ii) of the methods preferably comprises a step of homogenising the sample, as described below.

In particular, the sample is preferably not frozen prior to performing the present methods. The samples may if needed be stored at low temperatures for up to several weeks prior to analysis by the present methods, as storage has been found not to affect the phospholipid content as shown in the examples. For example, storage may be for 1 hour or more, such as 2 hours or more, such as 3 hours or more, such as 6 hours or more, such as 12 hours or more, such as 24 hours or more, such as 2 days or more, such as 3 days or more, such as 1 week or more, such as 2 weeks or more, such as 1 month. Storage is preferably at a temperature between 1 and 10° C., such as 2° C., 3° C., 4° C., 5° C., 6° C., 7° C., 8° C., 9° C. or 10° C., preferably at 4° C. or 5° C.

Homogenisation of the Sample

In step ii), the sample may be diluted and/or homogenised in a first solution. Homogenisation can be achieved as is known to the skilled person. For example, the sample may be placed on a vortex, thereby strongly stirring the sample. In some embodiments, the sample may be diluted prior to and/or after homogenisation.

The sample is diluted in a first volume of a first solution, preferably a hypotonic solution. The first solution may be water, such as deionized water, or tap water. In one embodiment of the method, the first solution is deionized water. In another embodiment, the first solution is plain water, such as tap water. Without being bound by theory, it is hypothesized that the first solution lyses the cells, thereby facilitating precipitation of lamellar bodies in the next steps of the method.

The volume of the first solution can vary, since the sample is precipitated in later steps of the method. The volume of the first solution should preferably be at least equal to half the volume of the sample, such as at least equal to the volume of the sample, such as at least equal to twice the volume of the sample, such as at least equal to three times the volume of the sample, such as at least equal to four times the volume of the sample, such as at least equal to five times the volume of the sample, such as at least equal to 6 times the volume of the sample, such as at least equal to 7 times the volume of the sample, such as at least equal to 8 times the volume of the sample, such as at least equal to 9 times the volume of the sample, such as at least equal to 10 times the volume of the sample, or more. Thus in one embodiment, the ratio of the volume of the sample of step i) to the volume of the first solution used in step 2 is 1:0.5. In another embodiment the ratio of the sample of step i) to the volume of the first solution used in step ii) is 1:1. In another embodiment the ratio of the sample of step i) to the volume of the first solution used in step ii) is 1:2. In another embodiment the ratio of the sample of step i) to the volume of the first solution used in step ii) is 1:3. In another embodiment the ratio of the sample of step i) to the volume of the first solution used in step ii) is 1:4. In another embodiment the ratio of the sample of step i) to the volume of the first solution used in step ii) is 1:5. In another embodiment the ratio of the sample of step i) to the volume of the first solution used in step ii) is 1:6. In another embodiment the ratio of the sample of step i) to the volume of the first solution used in step ii) is 1:7. In another embodiment the ratio of the sample of step i) to the volume of the first solution used in step ii) is 1:8. In another embodiment the ratio of the sample of step i) to the volume of the first solution used in step ii) is 1:9. In another embodiment the ratio of the sample of step i) to the volume of the first solution used in step ii) is 1:10.

After adding the volume of the first solution to the sample of step i), the sample and the first solution are mixed and homogenized, e.g. by vortexing or pipetting as is known to the skilled person, until the mixture appears homogenous to the naked eye. A homogenous sample is thereby obtained.

Precipitation of the Lamellar Bodies

In step iii) of the method, the homogenous sample obtained in step ii) is transferred to a centrifuge, and centrifugation is performed in order to obtain a pellet comprising lamellar bodies and a supernatant. In step iv), the supernatant is discarded.

Centrifugation is performed as is known in the art, at a force and for a duration sufficient to allow the lamellar bodies to be precipitated from the sample, so that a pellet is obtained comprising lamellar bodies. Without being bound by theory, centrifugation is thought to allow removal of substantially all or almost all the cellular debris.

Centrifugation may be performed at a force between 500 and 10000 g, such as between 1000 and 9000 g, such as between 2000 and 800 g, such as between 3000 and 7000 g, such as between 3500 and 6000 g, such as between 3750 and 5000 g, such as between 3750 and 4500 g, such as at about 4000 g. Centrifugation may be performed for a duration of 1 min to 10 min, such as 2 min to 9 min, such as 3 min to 8 min, such as 4 min to 7 min, such as 5 min to 6 min, such as 4 min, 5 min or 6 min.

For example, a centrifugation step of 4 minutes at 4000 g is suitable for performing the methods of the invention. Alternatively, the centrifugation may be for 2 minutes at 5000 g or more, for example 6000 g or more, for example 7000 g or more, for example 8000 g or more, for example 9000 g or more, for example 10000 g or more. The centrifugation may be for 10 minutes at 500 g or more, for example 1000 g or more, such as 2000 g or more, for example 3000 g or more, such as 4000 g or more, for example 5000 g or more, such as 6000 g or more, for example 7000 g or more, such as 8000 g or more, for example 9000 g or more, for example 10000 g.

Following centrifugation, the sample should now present two phases: a solid phase, or pellet, located at the bottom of the tube, and which may be invisible to the naked eye; and a liquid phase, or supernatant. The pellet comprises lamellar bodies from the sample in a concentrated form. The supernatant may also comprise a portion of lamellar bodies; however, the majority of lamellar bodies is preferably present in the pellet.

The supernatant is discarded as is known in the art. This may be done by pipetting the supernatant away, while being careful not to disturb the pellet, or it may be done by simply gently pouring the supernatant away, and optionally pipetting the remaining volume. The container in which the sample is comprised may be tipped gently and tapped gently on a piece of e.g. absorbing paper, in order to remove the small volumes of liquid which may remain on the walls of the container by gravity.

In some embodiments, the method is temperature-independent at least when performed in a temperature range between 20° C. and 40° C.

Analysis of the Sample

Once the pellet is essentially free of supernatant, it is resuspended in a volume of a second solution, so that a sample for analysis is obtained. The second solution may be a hypotonic solution or a saline solution. The second solution may be water, such as deionized water, or tap water. In one embodiment of the method, the second solution is saline solution. In another embodiment, the second solution is deionized water. In a third embodiment, the second solution is plain water, such as tap water.

The volume of second solution to be added to the pellet depends on the analysis means used in step v), and will be described in more detail below.

The sample for analysis is used to determine the amount of a first compound selected from lecithin and saturated lecithin, and optionally the amount of sphingomyelin. In one embodiment, the sample for analysis is used to determine the amount of a first compound selected from lecithin and saturated lecithin, and the amount of sphingomyelin. Without being bound by theory, it is thought that the amounts determined in this step are representative of the amounts present in the original sample, i.e. the sample provided in step i), or are at least proportional to the amounts present in the original sample. Accordingly, the concentration of the first compound in the sample for analysis is preferably equal to or substantially equal to the concentration of the same in the sample provided in step i), i.e. the sample obtained from a subject. The ratio of the first compound to sphingomyelin in the sample for analysis is preferably equal to or substantially equal to the ratio of the same in the sample provided in step i), i.e. the sample obtained from a subject. Said ratio will herein be termed L/S ratio.

In some embodiments, it may be desirable to remove at least part or all of the second solution after resuspension or prior to analysis. This can be done for example by evaporation of at least part or all of the second solution. In some embodiments, the method thus comprises a step of drying the sample after resuspension and/or prior to determining the amount of the first compound and/or of sphingomyelin.

The volume of sample for analysis suitable for determining the amounts of the first compound and optionally of sphingomyelin may vary. In one embodiment, the volume of sample for analysis suitable for determining the amounts of the first compound and of sphingomyelin may vary.

In some embodiments, the sample for analysis may be transferred to a $CaF_2$ window. Removal of at least part of the second solution may thus aptly be performed at the time of transfer, for example if the $CaF_2$ window is at a high temperature allowing for evaporation, such as 80° C. or more, such as 85° C., 86° C., 87° C., 88° C., 89° C., 90° C., 91° C., 92° C., 93° C., 94° C., 95° C. or more. Part of the second solution may also have been evaporated prior to this step, and in some embodiments the method thus comprises two steps of removing at least part of the second solution prior to determining the amounts of the first compound and/or sphingomyelin.

In some embodiments, the sample for analysis is analysed using an infrared spectrometer. In a particular embodiment, the analysis means is a Fourier transformed infrared spectrometer (FTIR). Preferably, the amounts of sphingomyelin and/or of the first compound are determined in the mid-wavelength infrared range. Preferably, the amounts of sphingomyelin and of the first compound are determined in the mid-wavelength infrared range.

Suitable sample volumes for spectrometer analysis, in particular FTIR analysis, may be between 10 and 200 μL, such as between 25 and 175 μL, such as between 50 and 150 μL, such as between 75 and 125 μL, such as 100 μL, 75 μL, 50 μL, or 25 μL.

The present methods allow determination of the concentration of lecithin or saturated lecithin and optionally of the L/S ratio by measuring the amount of lecithin and saturated lecithin and optionally of sphingomyelin and lecithin or saturated lecithin, respectively. In some embodiments, the present methods allow determination of the L/S ratio by measuring the amount of sphingomyelin and lecithin, or by measuring the amount of sphingomyelin and saturated lecithin. The methods may also further include determining the amount of a third compound. In some embodiments, the third compound is phosphatidylglycerol.

The amount of a compound can be measured as a concentration or as an activity, as the person of skill is well aware of. In some embodiments of the disclosure, the amount of a compound is thus its concentration and/or activity.

Once the amounts of lecithin or saturated lecithin and/or sphingomyelin have been determined, the concentration of lecithin or saturated lecithin is calculated and compared with a control value, and/or the L/S ratio is calculated and compared with a control ratio, as described below. In some embodiments, once the amounts of sphingomyelin and/or lecithin or saturated lecithin have been determined, the L/S ratio is calculated and compared with a control ratio, as described below.

Diagnostic

The concentration of lecithin or saturated lecithin in the lamellar bodies is compared in some embodiments to a control value. The control value is a threshold value, which corresponds substantially to the concentration of lecithin or saturated lecithin measured in subjects which do not suffer from RDS.

In some embodiments, the control value is 49.0 µmol/L±0.5 µmol/L, such as 49.0 µmol/L. A concentration of lecithin or saturated lecithin equal to or less than 49.0 µmol/L±0.5 µmol/L is indicative of the subject suffering from RDS. In this case, the subject may be treated as is known in the art, for example as described herein.

In some embodiments, the control value is between 45.0 µmol/L±0.5 µmol/L and 53 µmol/L±0.5 µmol/L, such as between 46.0 µmol/L±0.5 µmol/L and 52 µmol/L±0.5 µmol/L, such as between 47 µmol/L±0.5 µmol/L and 51 µmol/L±0.5 µmol/L, such as between 48 µmol/L±0.5 µmol/L and 50 µmol/L±0.5 µmol/L, such as 49.0 µmol/L±0.5 µmol/L.

Accordingly, if the concentration of lecithin or saturated lecithin in the lamellar bodies as measured by the methods disclosed herein is equal to or less than 55.0 µmol/L±0.5 µmol/L, such as less than 54.0 µmol/L±0.5 µmol/L, such as equal to or less than 53.0 µmol/L±0.5 µmol/L, such as equal to or less than 52.0 µmol/L±0.5 µmol/L, such as equal to or less than 51 µmol/L±0.5 µmol/L, such as equal to or less than 50.0 µmol/L±0.5 µmol/L, such as equal to or less than 49.0 µmol/L±0.5 µmol/L, the subject is classified as having or likely to have RDS. Preferably, the control value is 49.0 µmol/L±0.5 µmol/L, 50.0 µmol/L±0.5 µmol/L or 48.0 µmol/L±0.5 µmol/L.

In some embodiments, the L/S ratio in the sample is determined and compared to a control ratio. The control ratio is a threshold value, which corresponds substantially to the L/S ratio measured in subjects which do not suffer from RDS.

In some embodiments, the control ratio is between 1.0 and 2.5±0.5. An L/S ratio smaller than the control ratio is indicative of the subject suffering from RDS. In this case, the subject may be treated as is known in the art, for example as described herein.

The control ratio in some embodiments is between 2.0 and 4.0±0.5.

In some embodiments, the control ratio is between 1.0 and 3.0±0.5, such as between 1.5 and 2.9±0.5, such as between 2.0 and 2.8±0.5, such as between 2.2 and 2.7±0.5, such as between 2.4 and 2.6±0.5, such as 2.5±0.5 or 2.0±0.5. In some embodiments, the control ratio is between 2.0 and 5.0±0.5, such as between 2.2 and 4.5±0.5, such as between 2.4 and 4.0±0.5, such as between 2.6 and 3.5±0.5, such as between 2.8 and 3.2±0.5, such as 3±0.5.

Accordingly, if the L/S ratio in the lamellar bodies as measured by the methods disclosed herein is equal to or less than 1.0±0.5, such as equal to or less than 1.2±0.5, such as equal to or less than 1.5±0.5, such as equal to or less than 1.7±0.5, such as equal to or less than 2.0±0.5, such as equal to or less than 2.2±0.5, such as equal to or less than 2.5±0.5, the subject is classified as having or likely to have RDS. Preferably, the control ratio is 2.0±0.5, 2.5±0.5 or 3.0±0.5. In other embodiments, if the L/S ratio in the lamellar bodies as measured by the methods disclosed herein is equal to or less than 2.5±0.5, such as equal to or less than 2.6±0.5, such as equal to or less than 2.7±0.5, such as equal to or less than 2.8±0.5, such as equal to or less than 2.9±0.5, such as equal to or less than 3.0±0.5, the subject is classified as having or likely to have RDS. In some embodiments, if the L/S ratio in the lamellar bodies as measured by the methods disclosed herein is less than 1.0±0.5, such as less than 1.2±0.5, such as less than 1.5±0.5, such as less than 1.7±0.5, such as less than 2.0±0.5, such as less than 2.2±0.5, such as less than 2.5±0.5, the subject is classified as having or likely to have RDS. Preferably, the control ratio is 2.0±0.5, 2.5±0.5 or 3.0±0.5. In other embodiments, if the L/S ratio in the lamellar bodies as measured by the methods disclosed herein is equal to or less than 2.5±0.5, such as equal to or less than 2.6±0.5, such as equal to or less than 2.7±0.5, such as equal to or less than 2.8±0.5, such as equal to or less than 2.9±0.5, such as equal to or less than 3.0±0.5, the subject is classified as having or likely to have RDS. In some embodiments, if the L/S ratio in the lamellar bodies as measured by the methods disclosed herein is less than 2.5±0.5, such as less than 2.6±0.5, such as less than 2.7±0.5, such as less than 2.8±0.5, such as less than 2.9±0.5, such as less than 3.0±0.5, the subject is classified as having or likely to have RDS.

The present methods preferably have a specificity of 50 or more, such as 60 or more, such as 70 or more, such as 80 or more, such as 90 or more. The present methods preferably have a sensitivity of 50 or more, such as 60 or more, such as 70 or more, such as 80 or more, such as 90 or more.

The present methods may be performed fast, and are thus well suited for point-of-care units. In some embodiments, the time-to-result of the method is between 5 and 60 minutes, such as between 10 and 50 minutes, such as between 20 and 40 minutes, such as between 25 and 35 minutes, such as about 30 minutes. In some embodiments, the time-to-result of the method is 60 minutes or less, such as 55 minutes or less, such as 50 minutes or less, such as 45 minutes or less, such as 40 minutes or less, such as 35 minutes or less, such as 30 minutes or less, such as 25 minutes or less, such as 20 minutes or less, such as 15 minute or less, such as 10 minutes or less, such as 5 minutes or less.

The time-to-result is herein defined as the time between steps i) and step vi) of the methods.

In some embodiments, only the concentration of lecithin or saturated lecithin is determined and compared to a control value as described above. In other embodiments, the concentration of lecithin or saturated lecithin and the concentration of sphingomyelin are determined, the L/S ratio is calculated and compared to a control ratio as described above. In some embodiments, the concentration of lecithin or saturated lecithin is determined and compared to a control value and the concentration of sphingomyelin is also determined to calculate the L/S ratio which is compared to a control ratio.

Method of Treatment of RDS

Any of the embodiments disclosed herein, i.e. any of the methods described above, may further include a step of treating a subject classified as having or likely to have RDS. In some embodiments, the treatment is administration of a therapeutically effective amount of surfactant to the subject. Preferably, the subject is a newborn individual.

Accordingly, also disclosed herein is a method of treatment of Respiratory Distress Syndrome (RDS) in a newborn individual, comprising the steps of:
  i) providing a sample, such as an amniotic fluid sample, a blood sample, an oropharyngeal secretion sample or a gastric aspirate sample, from said newborn individual;
  ii) diluting and homogenising said sample in a first volume of a first solution, thereby obtaining a homogenous sample;
  iii) centrifuging the homogenous sample to obtain a pellet comprising lamellar bodies and a supernatant;
  iv) discarding the supernatant and resuspending the pellet in a second volume of a second solution, thereby obtaining a sample for analysis;
  v) determining the amount of a first compound selected from lecithin and saturated lecithin and optionally the amount of sphingomyelin in the sample for analysis, using analysis means;

vi) obtaining a concentration of the first compound and optionally a ratio between the first compound and sphingomyelin;

vii) correlating the concentration of vi) with a control value and optionally correlating the ratio of vi) with a control ratio, wherein a concentration differing from the control value and optionally a ratio differing from the control ratio is indicative of Respiratory Distress Syndrome (RDS) of the subject;

viii) if the concentration of vi) is equal to or less than the control value and/or if the ratio of vi) is equal to or less than the control ratio, administering a therapeutically effective amount of surfactant to the newborn individual.

Also disclosed herein is a method of treatment of Respiratory Distress Syndrome (RDS) in a newborn individual, comprising the steps of:

i) providing a gastric aspirate sample from said newborn individual;

ii) diluting and homogenising said sample in a first volume of a first solution, thereby obtaining a homogenous sample;

iii) centrifuging the homogenous sample to obtain a pellet comprising lamellar bodies and a supernatant;

iv) discarding the supernatant and resuspending the pellet in a second volume of a second solution, thereby obtaining a sample for analysis;

v) determining the amount of a first compound selected from lecithin and saturated lecithin and the amount of sphingomyelin in the sample for analysis, using analysis means;

vi) obtaining a ratio between the first compound and sphingomyelin;

vii) correlating the ratio of vi) with a control ratio, wherein a ratio differing from the control ratio is indicative of Respiratory Distress Syndrome (RDS) of the subject;

viii) if the ratio of vi) is less than the control ratio, administering a therapeutically effective amount of surfactant to the newborn individual.

The control value and the control ratio are as defined in the section entitled "diagnostic" above.

Based on the diagnostic methods outlined herein above a rapid treatment of the individual in need thereof can be achieved, thus resulting in improved survival rate of the individual. The invention is in particular well suited for diagnosing and treating a newborn such as a premature infant.

Computer Implemented Method and Systems for Diagnosing RDS

In one aspect, the invention concerns a computer implemented method for diagnosing RDS based on spectral data acquired from a sample, wherein the sample is a gastric aspirate sample, a blood sample, an orpharyngeal sample or an amniotic fluid samples obtained from a subject, the method comprising the steps of:

i) determining the activity and/or concentration of a first compound selected from lecithin and saturated lecithin and optionally of sphingomyelin in said sample by acquiring spectral data for the sample, ii) optionally calculating a ratio between the activities and/or concentrations of sphingomyelin and of the first compound, iii) correlating said concentration with a control value and optionally correlating said ratio with a control ratio, wherein a concentration equal to or lower than the control value and/or a ratio equal to or lower than the control ratio is indicative of RDS of the subject.

In another aspect, the invention concerns a computer implemented method for diagnosing RDS based on spectral data acquired from a sample, wherein the sample is a gastric aspirate sample, an orpharyngeal sample or an amniotic fluid samples obtained from a subject, the method comprising the steps of:

i) determining the activity and/or concentration of sphingomyelin and of a first compound selected from lecithin and saturated lecithin in said sample by acquiring spectral data for the sample, ii) calculating a ratio between the activities and/or concentrations of sphingomyelin and of the first compound, iii) correlating said ratio with a control ratio, wherein a ratio differing from the control ratio is indicative of RDS of the subject.

Steps i), ii) and iii) may be performed by any of the methods described herein above.

The control value and the control ratio are as defined in the section entitled "diagnostic" above.

As time may be an important factor for treating RDS, the computer-implemented diagnosis method may advantageously be integrated in a diagnosis system that can be installed in hospital departments, such as the neonatal department, preferably in the delivery room. Such a system can integrate spectroscopy, analysis and disease indication that may provide a diagnostic within minutes after a biological sample has been obtained. Accordingly is provided herein a system for diagnosing RDS based on a sample obtained from said subject, wherein the sample is an amniotic fluid sample, a blood sample, an orpharyngeal secretion or a gastric aspirate sample, comprising a spectroscope for measuring spectral data from said sample, processing means configured for a) determining the activity and/or concentration of a first compound selected from lecithin and saturated lecithin and/or of sphingomyelin in said sample by analysing said spectral data, b) calculating a concentration of the first compound and optionally a ratio between the activities and/or concentrations of the first compound and sphingomyelin, and c) correlating said concentration with a control concentration and optionally correlating said ratio with a control ratio, and d) indicating whether the concentration is equal to or lower than the control value and optionally indicating if the ratio is equal to or lower than the control ratio, wherein a predefined difference is indicative of Respiratory Distress Syndrome (RDS) of the subject.

Also provided herein is a system for diagnosing RDS based on a sample obtained from said subject, wherein the sample is an amniotic fluid sample, an orpharyngeal secretion or a gastric aspirate sample, comprising a spectroscope for measuring spectral data from said sample, processing means configured for a) determining the activity and/or concentration of sphingomyelin and of a first compound selected from lecithin and saturated lecithin in said sample by analysing said spectral data, b) calculating a ratio between the activities and/or concentrations of lecithin and the first compound, and c) correlating said ratio with a control ratio, and indicating whether the ratio is different from the control ratio, wherein a predefined difference is indicative of Respiratory Distress Syndrome (RDS) of the subject.

Thus, the present method may be integrated in a personal computer or it may be effectuated from a website, mobile phone, smartphone or other electronic device capable of executing computer code. A further embodiment of the invention therefore relates to a computer program product having a computer readable medium, said computer program product being suitable for diagnosing a respiratory disease of a subject based on spectral data acquired from a sample obtained from said subject, said computer program product comprising means for carrying out all the steps of the herein disclosed method, wherein the sample is a gastric aspirate sample, a blood sample, an amniotic fluid sample or an oropharyngeal secretion sample.

In one embodiment, the sample is a gastric aspirate sample. In another embodiment, the sample is an amniotic fluid sample. In another embodiment, the sample is an oropharyngeal secretion. In another embodiment, the sample is a blood sample.

The system may be part of a health monitoring system as described in WO 2008/019695 disclosing a health monitoring service based on a central server, wherein the measurement of the samples is carried out as a local measurement and the measurement data are subsequently sent to a central server, where the data are processed and analysed, for example by expert knowledge systems, and a health profile is generated and sent back to the local system. Thus, the processing means may be fully or partly integrated in a central service remote from the local hospital department or even remote from the hospital. However, the processing means may also be fully integrated in the local system such that the system located in the hospital department includes spectrometer, spectral analysis and processing and disease indication.

REFERENCES

1. Dorland's Medical Dictionary—"Neonatal respiratory distress syndrome"
2. Rodriguez R J, Martin R J, and Fanaroff, A A. (2002) Neonatal-perinatal medicine: Diseases of the fetus and infant; 7th ed. (2002):1001-1011. St. Louis: Mosby.
3. Kamper J, Wulff K, Larsen C, Lindequist S. (1993) Acta Paediatr; 82:193-197.
4. Polin R A, Sahni R. (2002) Semin Neonatol 7:739-789.
5. Verder H. (2007) Acta Pdiatr 96:482-484.
6. Verder H, Albertsen P, Ebbesen F, Greisen G, Robertson B, Bertelsen A, Agertoft L, Djernes B, Nathan E, Reinholdt J. (1999) Pediatrics 103:e24.
7. Sandri F, Plavka R, Ancora G, Simeoni U, Stranak Z, Martinelli S, Mosca F, Nona J, Thomson, M, Verder H, Fabbri L, Halliday H. (2010) Pediatrics 125:e140.
8. Bevilacqua G, Parmagiani S, Robertson B. (1996) J Perinat Med 24:1-12.
9. Verder H., "Prnatal bestemmelse af lungematuriteten og forebyggelse af idiopatisk respiratory distress syndrom. Lecithinsphingomyelin ratio i amnionvæsken" Doctoral dissertation 27 Nov. 1980 at University of Copenhagen.
10. Soll R F. (1999) Cochrane Database Syst Rev 4:CD001456.
11. Stevens T P, Blennow M, Meyers E H, Soll R. (2007) Cochrane Database Syst Rev 2007; 4: CD003063.
12. Verder H, Robertson B, Greisen G, Ebbesen F, Albertsen P, Lundstrøm K, Jacobsen T. (1994) N Engl J Med 331:1051-1055.
13. Soll R F. (2012) Neonatology 102:169-171.
14. Van Kaam A H, Jaegere A P, Borensztajn D, Rimensberger P C (2011) Neonatology 100:71-77.
15. Liu K-Z, Dembinski T C, Mantsch H H (1998) Prenatal Diagnosis 18: 1267-1275
16. Verder H, Heiring C, Clark H, Sweet D, Jessen T E, Ebbesen F, Björklund LJ, Andreasson B, Bender L, Bertelsen A, Dahl M, Eschen C, Fenger-Grøn J, Hoffmann S F, Höskuldsson A, Brussgaard-Mouritsen M, Lundberg F, Postle A D, Schousboe P, Schmidt P, Stanchev H, Sorensen L (2017) Acta Paediatr. 2017 March; 106(3): 430-437

Items

1. A method for diagnosing Respiratory Distress Syndrome (RDS) in a subject, the method comprising the steps of:
   i) providing a sample from said subject, wherein the sample is an amniotic fluid sample, a blood sample, an oropharyngeal secretion sample or a gastric aspirate sample;
   ii) homogenising and diluting said sample in a first volume of a first solution, thereby obtaining a homogenous sample;
   iii) centrifuging the sample of step ii) to obtain a pellet comprising lamellar bodies, and a supernatant;
   iv) discarding the supernatant and resuspending the pellet in a second volume of a second solution, thereby obtaining a sample for analysis;
   v) determining the amount of a first compound selected from lecithin and saturated lecithin and optionally the amount of sphingomyelin in the sample for analysis, using analysis means;
   vi) obtaining a concentration of the first compound and/or a ratio between the first compound and sphingomyelin;
   vii) the concentration of vi) with a control value, wherein a concentration equal to or lower than the control value is indicative of the subject having Respiratory Distress Syndrome (RDS); and/or correlating the ratio of vi) with a control ratio, wherein a ratio equal to or lower than the control ratio is indicative of the subject having Respiratory Distress Syndrome (RDS).

2. The method of item 1, comprising the steps of:
   i) providing a sample from said subject, wherein the sample is an amniotic fluid sample, an oropharyngeal secretion sample or a gastric aspirate sample;
   ii) homogenising and diluting said sample in a first volume of a first solution, thereby obtaining a homogenous sample;
   iii) centrifuging the sample of step ii) to obtain a pellet comprising lamellar bodies, and a supernatant;
   iv) discarding the supernatant and resuspending the pellet in a second volume of a second solution, thereby obtaining a sample for analysis;
   v) determining the amount of a first compound selected from lecithin and saturated lecithin and the amount of sphingomyelin in the sample for analysis, using analysis means;
   vi) obtaining a ratio between the first compound and sphingomyelin;
   vii) correlating the ratio of vi) with a control ratio, wherein a ratio differing from the control ratio is indicative of the subject having Respiratory Distress Syndrome (RDS).

3. The method according to any one of the preceding items, wherein the sample has a volume between 10 and 1000 μL, such as between 10 and 750 μL, such as between 20 and 500 μL, such as between 30 and 250 μL, such as between 40 and 125 μL, such as between 50 and 100 μL, such as between 60 and 90 μL, such as between 70 and 80 μL, such as 50 μL, 75 μL or 100 μL.
4. The method according to any one of the preceding items, wherein the sample provided in step i) is homogenous.
5. The method according to any one of the preceding items, wherein the first solution is a hypotonic solution or saline solution.
6. The method according to item 5, wherein the first solution is a hypotonic solution such as water or deionised water.
7. The method according to item 5, wherein the first solution is saline solution.
8. The method according to any one of the preceding items, wherein the ratio of the volume of the sample of step i) to the volume of the first solution used in step ii) is between 1:1 and 1:10, such as 1:1, 1:2, 1:3, 1:4, 1:5, 1:6, 1:7, 1:8, 1:9 or 1:10, preferably 1:4 or 1:6.
9. The method according to any one of the preceding items, wherein homogenising in step ii) is performed by pipetting repeatedly or vortexing.
10. The method according to any one of the preceding items, wherein the centrifugation of step iii) is performed at a force between 500 and 10000 g, such as 4000 g.
11. The method according to any one of the preceding items, wherein the centrifugation of step iii) is performed for a duration of 1 min to 10 min, such as 2 min to 9 min, such as 3 min to 8 min, such as 4 min to 7 min, such as 5 min to 6 min, such as 4 min, 5 min or 6 min.
12. The method according to any of the preceding items, wherein the centrifugation of step iii) is performed at 4000 g for 4 min.
13. The method according to any one of the preceding items, wherein discarding the supernatant in step iv) is performed by pipetting the supernatant or by pouring away the supernatant.
14. The method according to any one of the preceding items, wherein resuspending the pellet in step iv) is performed by pipetting repeatedly or vortexing.
15. The method according to any one of the preceding items, wherein the second solution is a hypotonic solution.
16. The method according to item 15, wherein the second solution is a hypotonic solution such as water or deionised water.
17. The method according to any one of the preceding items, wherein the second volume is between 10 and 200 μL, such as between 25 and 175 μL, such as between 50 and 150 μL, such as between 75 and 125 μL, such as 100 μL, 75 μL, 50 μL, or 25 μL.
18. The method according to any one of the preceding items, wherein step iv) further comprises a step of drying the sample after resuspension, whereby the second solution is at least partially removed by evaporation.
19. The method according to any one of the preceding items, wherein step v) further comprises a step of drying the sample prior to determining the amount of the first compound.
20. The method according to any one of the preceding items, wherein step v) further comprises a step of transferring the sample for analysis to a support structure such as a $CaF_2$ window, optionally wherein the support structure is at a temperature allowing for at least partial evaporation of the second solution, such as 90° C.
21. The method according to any one of the preceding items, wherein the analysis means is selected an infrared spectrometer, such as a Fourier transformed infrared (FTIR) spectrometer.
22. The method according to any one of the preceding items wherein the analysis means is an FTIR spectrometer.
23. The method according to any one of the preceding items, wherein the amount of the first compound and optionally the amount of sphingomyelin are determined in the mid-wavelength infrared range.
24. The method according to any one of the preceding items, further comprising determining the amount of a further compound.
25. The method according to any one of the preceding items, wherein the further compound is phosphatidylglycerol.
26. The method according to any one of the preceding items, wherein the amount of the first compound, of sphingomyelin and/or of the further compound is determined by measuring their activity and/or concentration.
27. The method according to any one of the preceding items, wherein the method is temperature-independent, at least in the range of 20° C. to 40° C.
28. The method according to any one of the preceding items wherein the subject is a human being.
29. The method according to any one of the preceding items wherein the human being is an infant.
30. The method according to any one of the preceding items wherein the infant is a newborn.
31. The method according to any one of the preceding items wherein the infant is a premature infant.
32. The method according to any one of the preceding items wherein the premature infant is born at between 20 and 42 weeks gestation, such as between 20 and 41 weeks, such as between 20 and 40 weeks, such as between 20 and 39 weeks gestation, such as between 21 and 38 weeks, such as between 23 and 37 weeks, such as between 24 and 37 weeks, such as between 25 and 37 weeks, such as between 26 and 37 weeks, such as between 27 and 37 weeks, such as between 28 and 37 weeks, such as between 29 and 38 weeks, such as between 30 and 39 weeks, such as between 31 and 39 weeks, such as between 32 and 39 weeks, such as between 33 and 39 weeks, such as between 34 and 39 weeks, such as between 35 and 39 weeks, such as between 36 and 39 weeks, such as between 37 and 39 weeks, such as between 38 and 39 weeks, such as between 38 and 40 weeks such, such as between 38 and 41 weeks, such as between 38 and 42 weeks, such as before 43 weeks gestation.
33. The method according to any one of the preceding items wherein the sample has been obtained from a newborn less than 24 h postnatal, preferably less than 20 h postnatal, more preferably less than 12 h postnatal, more preferably less than 5 h postnatal, more preferably less than 4 h postnatal, more preferably less than 3 h postnatal, more preferably less than 2 h postnatal, more preferably less than 1 h postnatal, more preferably less than 30 minutes postnatal, more preferably less than 20 minutes postnatal, more preferably less than 10 minutes postnatal, more preferably less than 5 minutes postnatal, more preferably less than 4 minutes postnatal, more preferably less than 3 minutes postnatal, more preferably less than 2 minutes postnatal, more preferably less than 1 minute postnatal.
34. The method according to any one of the preceding items, wherein the sample is a gastric aspirate sample.
35. The method according to any one of items 1 to 34, wherein the sample is amniotic fluid.
36. The method according to item 35, wherein the subject is a female human being.
37. The method according to any one of items 35 to 36, wherein the female is a pregnant female.
38. The method according to any one of items 35 to 37, wherein the female is a female undergoing, or immediately about to undergo, caesarean sectioning.
39. The method according to any one of items 35 to 38, wherein the body fluid sample is amniotic fluid collected from the female during or immediately subsequent to the caesarean sectioning.
40. The method according to any one of the preceding items, wherein the time-to-result of the method is between 5 and 60 minutes, such as between 8 and 30 minutes, such as 15 minutes.
41. The method according to any one of the preceding items, wherein the control ratio is between 1.0 and 3.0±0.5, such as between 1.5 and 2.9±0.5, such as between 2.0 and 2.8±0.5, such as between 2.2 and 2.7±0.5, such as between 2.4 and 2.6±0.5, such as 2.5±0.5 or 2.0±0.5.
42. The method according to any one of the preceding items, wherein the control ratio is between 2.0 and 5.0±0.5, such as between 2.2 and 4.5±0.5, such as between 2.4 and 4.0±0.5, such as between 2.6 and 3.5±0.5, such as between 2.8 and 3.2±0.5, such as 3±0.5.
43. The method according to any one of the preceding items, wherein if the ratio of step vi) is equal to or less than 3.0±0.5, equal to or less than 2.5±0.5 or equal to or less than 2.0±0.5, the subject is classified as having or likely to have RDS.
44. The method according to any one of the preceding items, wherein if the concentration of vi) is equal to or less than 49.0 µmol/L±0.5 µmol/L, the subject is classified as having or likely to have RDS.
45. The method according to any one of the preceding items, wherein the method has a specificity of 50 or more, such as 60 or more, such as 70 or more, such as 80 or more, such as 90 or more.
46. The method according to any one of the preceding items, wherein the method has a sensitivity of 50 or more, such as 60 or more, such as 70 or more, such as 80 or more, such as 90 or more.
47. A method of treatment of Respiratory Distress Syndrome (RDS) in a newborn individual, comprising the steps of:
i) providing a sample from said newborn individual, wherein the sample is an amniotic fluid sample, a blood sample, an oropharyngeal secretion sample or a gastric aspirate sample;
ii) diluting and homogenising said sample in a first volume of a first solution, thereby obtaining a homogenous sample;
iii) centrifuging the homogenous sample to obtain a pellet comprising lamellar bodies and a supernatant;
iv) discarding the supernatant and resuspending the pellet in a second volume of a second solution, thereby obtaining a sample for analysis;
v) determining the amount of a first compound selected from lecithin and saturated lecithin and optionally the amount of sphingomyelin in the sample for analysis, using analysis means;
vi) obtaining a concentration of the first compound and optionally a ratio between the first compound and sphingomyelin;
vii) correlating the concentration of vi) with a control value, wherein a concentration equal to or lower than the control value is indicative of the subject having Respiratory Distress Syndrome (RDS); and/or correlating the ratio of vi) with a control ratio, wherein a ratio equal to or lower than the control ratio is indicative of the subject having Respiratory Distress Syndrome (RDS);
viii) if the concentration of vi) is equal to or less than the control value and/or if the ratio of vi) is equal to or less than the control ratio, administering a therapeutically effective amount of surfactant to the newborn individual.
48. The method according to item 47, comprising the steps of:
i) providing a sample from said newborn individual, wherein the sample is an amniotic fluid sample, an oropharyngeal secretion sample or a gastric aspirate sample;
ii) diluting and homogenising said sample in a first volume of a first solution, thereby obtaining a homogenous sample;
iii) centrifuging the homogenous sample to obtain a pellet comprising lamellar bodies and a supernatant;
iv) discarding the supernatant and resuspending the pellet in a second volume of a second solution, thereby obtaining a sample for analysis;
v) determining the amount of a first compound selected from lecithin and saturated lecithin and the amount of sphingomyelin in the sample for analysis, using analysis means;
vi) obtaining a ratio between the first compound and sphingomyelin;
vii) correlating the ratio of vi) with a control ratio, wherein a ratio differing from the control ratio is indicative of Respiratory Distress Syndrome (RDS) of the subject;
viii) if the ratio of vi) is less than the control ratio, administering a therapeutically effective amount of surfactant to the newborn individual.
49. The method according to any one of items 47 to 48, wherein steps i) to vii) are performed as defined in any one of items 1 to 46.
50. The method according to any one of items 47 to 49, wherein the control ratio is between 1.0 and 3.0±0.5, such as between 1.5 and 2.9±0.5, such as between 2.0 and 2.8±0.5, such as between 2.2 and 2.7±0.5, such as between 2.4 and 2.6±0.5, such as 2.5±0.5 or 2.0±0.5.
51. The method according to any one of items 47 to 50, wherein the control ratio is between 2.0 and 5.0±0.5, such as between 2.2 and 4.5±0.5, such as between 2.4 and 4.0±0.5, such as between 2.6 and 3.5±0.5, such as between 2.8 and 3.2±0.5, such as 3±0.5.
52. The method according to any one of items 47 to 51, wherein the control value is 49.0 µmol/L±0.5 µmol/L.
53. A computer implemented method for diagnosing RDS based on spectral data acquired from a sample obtained from a subject, wherein the sample is an amniotic fluid sample, a blood sample, an oropharyngeal secretion sample or a gastric aspirate sample, the method comprising the steps of:
i) determining the activity and/or concentration of a first compound selected from lecithin and saturated lecithin and optionally of sphingomyelin in said sample by acquiring spectral data for the sample,
ii) optionally calculating a ratio between the activities and/or concentrations of sphingomyelin and of the first compound,
iii) correlating said concentration with a control value and optionally correlating said ratio with a control ratio, wherein a concentration equal to or lower than the control value and/or a ratio equal to or lower than the control ratio is indicative of RDS of the subject.
54. The computer implemented method of item 53, comprising the steps of: i) determining the activity and/or concentration of sphingomyelin and of a first compound selected from lecithin and saturated lecithin in said sample by acquiring spectral data for the sample,
ii) calculating a ratio between the activities and/or concentrations of sphingomyelin and of the first compound,
iii) correlating said ratio with a control ratio, wherein a ratio differing from the control ratio is indicative of RDS of the subject.
55. The method according to any one of items 53 to 54, further comprising the features of any of items 1 to 46.
56. A computer program product having a computer readable medium, said computer program product suitable for diagnosing RDS of a subject based on spectral data acquired from a sample obtained from said subject, wherein the sample is an amniotic fluid sample, a blood sample, an oropharyngeal secretion sample or a gastric aspirate sample, said computer program product comprising means for carrying out all the steps of the method as defined in any of items 53 to 55.
57. A system for diagnosing RDS based on a sample obtained from said subject, wherein the sample is an amniotic fluid sample, a blood sample, an oropharyngeal secretion sample or a gastric aspirate sample, comprising
a spectroscope for measuring spectral data from said sample,
processing means configured for
a) determining the activity and/or concentration of a first compound selected from lecithin and saturated lecithin and/or of sphingomyelin in said sample by analysing said spectral data,
b) calculating a concentration of the first compound and optionally a ratio between the activities and/or concentrations of lecithin and the first compound, and
c) correlating said concentration with a control concentration and optionally said ratio with a control ratio, and
d) indicating whether the ratio is equal to or lower than the control value and optionally indicating if the ratio is equal to or lower than the control ratio, wherein a predefined difference is indicative of Respiratory Distress Syndrome (RDS) of the subject.
The system of item 57, wherein the processing means are configured for:
a) determining the activity and/or concentration of sphingomyelin and of a first compound selected from lecithin and saturated lecithin in said sample by analysing said spectral data,
b) calculating a ratio between the activities and/or concentrations of lecithin and the first compound, and
c) correlating said ratio with a control ratio, and
d) indicating whether the ratio is differing from the control ratio, wherein a predefined difference is indicative of Respiratory Distress Syndrome (RDS) of the subject.

EXAMPLES

A diagnostic test for lung maturity for optimal treatment of respiratory distress syndrome (RDS) has previously been developed based on mid-infrared spectroscopy on gastric aspirates (GAS) [16]. The study was based on analyses of lecithin/sphingomyelin (SM) raiot (L/S) on frozen and thawed GAS. Lecithin was measured as dipalmitoylphosphatidylcholine (DPPC).

In the present study, analyses were performed on fresh GAS. The spectroscopy signal has been enhanced by concentrating the surfactant and problems with interfering proteins, salts and mucus-like, flocculent protein cloths have been avoided.

The method is based on FTIR technology to analyse the contents of precipitated lamellar bodies. Stable measurements by dry transmission require a short path length for the infrared beam passing through the sample. The method if thus focused on removing irrelevant and excess material such as proteins and salts, resulting in improving purity of the lamellar bodies to be analysed.

Methods

GAS obtained immediately after birth were stored at 4° C. and analysed; some samples were analysed immediately, some were analysed within a few hours, others a few days, with a maximal storage of 2 weeks.

The L/S algorithm was built on 85 GAS (DPPC (55 samples) and SM (85 samples)) obtained from infants with gestational age 24-36 weeks. Sampling for FTIR and reference samples were obtained by standard methods. 200 µL GAS were diluted 4 fold with water and centrifuged at 4000 g for 4 minutes. After removal of the supernatant, the samples were resuspended in 100 µL of water and split in 2 aliquots of 50 µL. One aliquot was analysed by FTIR, and one aliquot was analysed by mass spectrocscopy (MS) for measuring contents in phosphatidylcholine (PC) and sphingomyelin. MS was performed as described in [16].

Dry transmission of samples was performed on $CaF_2$ windows (1 mm thick, 13 mm in diameter, Chrystran). The 50 µL samples were applied onto the $CaF_2$ windows dried on a hotplate (90° C.). The FTIR measurements were performed with Bruker Tensor 27, equipped with a DTGS detector (60 scans, resolution 4 $cm^{-1}$).

Pellets from treated samples were fixated in 4% paraformaldehyde until preparation for electron microscopy scanning.

Results

Viscosity of Frozen and Fresh Samples

Fresh, frozen and thawed GAS were compared in 30 cases. The mucus-like, flocculent material composed of phospholipids, proteins and mucus appeared mainly to be a consequence of freezing and was observed in both the frozen and the thawed material. These clot-like structures were mostly insoluble in contrast to fresh gastric aspirates which despite a high viscosity did not display clot formation, and could be dissolved and diluted (FIG. 1).

Mass Spectroscopy of Proteins and Phospholipids

Figure 2:
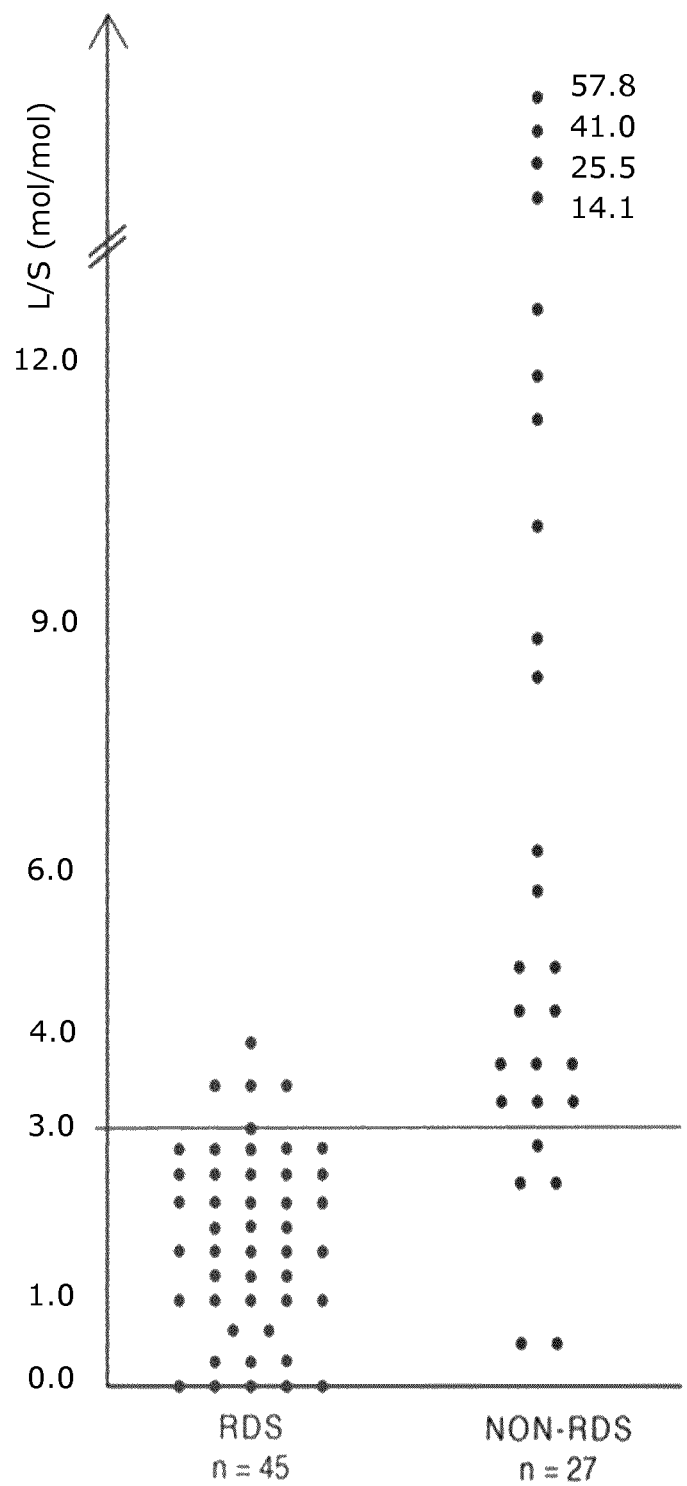
FIG. 2 Analysis of crude GAS and purified LB fractions analysed by MS show high correlations between L/S ratio and RDS. The horizontal line shows an appropriate cut-off value (3.0) for determining whether a newborn suffers from RDS. Sensitivity of the method is 91%, and specificity is 81%.

MS of proteins and phospholipids revealed that the mucus-like, flocculent material was consisting of a wide range of proteins and phospholipids. Protein content showed that mucus-like was dominant in the GAS. Further analysis also showed a high concentration of phospholipids. However, analysis of crude GAS and purified LB fractions analysed by MS show high correlations (FIG. 2).

Stability of Phospholipids During Storage

Four fresh GAS from newborns with various gestational age were included. The PC and SM contents were measured by MS at birth and again after storage for four weeks at 4-5° C. The phospholipids were stable and unchanged during the period.

Electron Microscopy

Figure 3:
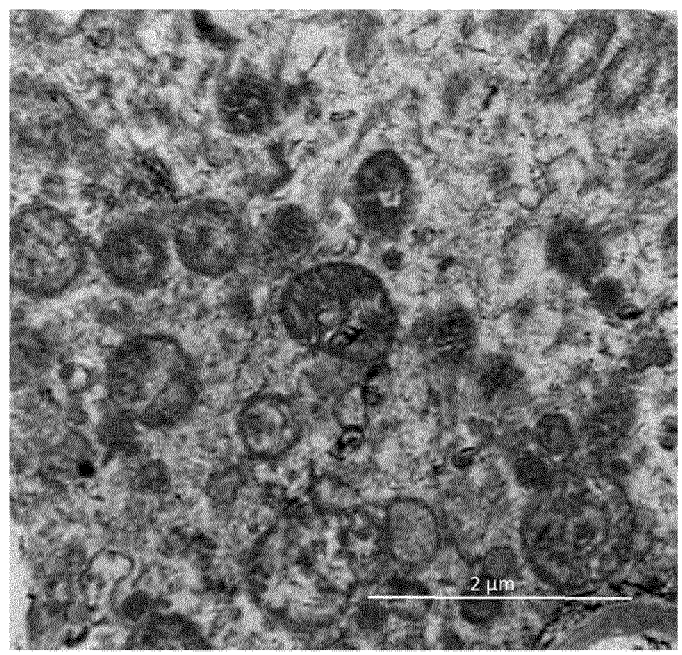
FIG. 3 Upper panel: electron microscopy of precipitated lamellar bodies from GAS at birth. Lower panel: lamellar bodies from GAS in large electron microscopy magnification.
Figure 3:
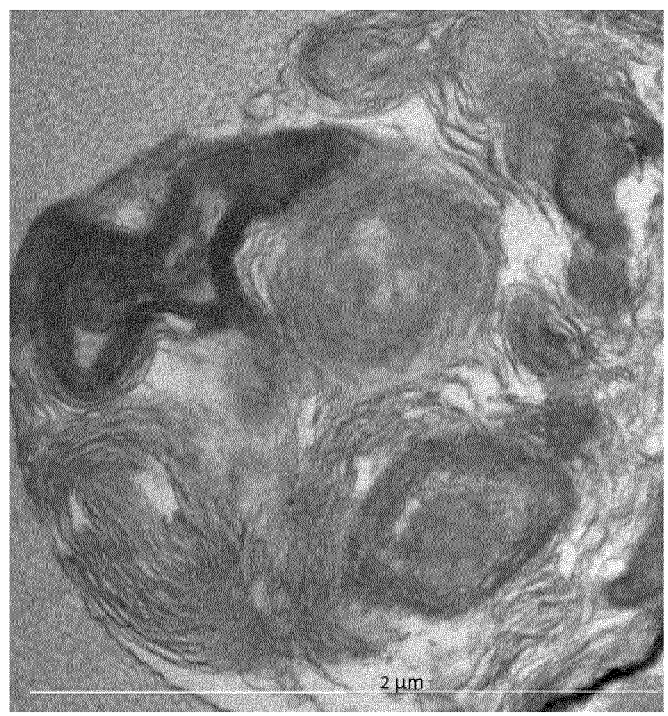

The lamellar bodies were visualized by electron microscopy (FIG. 3). Pellets obtained from GAS diluted with water showed lamellar body structures in samples from neonates at various gestational ages.

Sensitivity and Specificity

The present method shows a sensitivity of 91% and a specificity of 79% based on 72 neonate GAS. By comparison, diagnosis on a cut-off value (control ratio) for the L/S ratio of 3.0 and DPPC contents alone has a sensitivity of 93% and a specificity of 74%.

Blood Samples

The method was also applied to blood samples. The present method appears to reduce uncertainties as the blood cells during the hypotonic conditions burst and are removed along with the supernatant. MS of phospholipids indicated that most PC and SM originate from lamellar bodies.

CONCLUSION

We have developed a method for use with dry transmission that reduces salt and protein contents in the samples, thus resulting in stable and reliable measurements. Dilution of the samples lowers the viscosity of the allowing lamellar bodies to be precipitated by centrifugation at low g-force, where most cellular debris, proteins and salts remain in the supernatant. These improvements leave a smaller amount of more relevant material in the form of lamellar bodies carrying the surfactant. Water is evaporated by drying the samples, for example on a hotplate. Furthermore, the method is temperature independent, at least in the range of 20 to 40° C.

Using an appropriate spectroscope, lung maturity can thus be measured and determined within the first 10 to 15 minutes of life, with high specificity and sensitivity.

The invention claimed is:

1. A method for diagnosing Respiratory Distress Syndrome (RDS) in a subject, the method comprising the steps of:
   i) providing a sample from said subject, wherein the sample is an amniotic fluid sample, a blood sample, an oropharyngeal secretion sample or a gastric aspirate sample;
   ii) homogenising and diluting said sample in a first volume of a first solution, thereby obtaining a homogenous sample;
   iii) centrifuging the sample of step ii) to obtain a pellet comprising lamellar bodies, and a supernatant;
   iv) discarding the supernatant and resuspending the pellet in a second volume of a second solution, thereby obtaining a sample for analysis;
   v) determining the amount of a first compound selected from lecithin and saturated lecithin or determining the amount of a first compound selected from lecithin and saturated lecithin and the amount of sphingomyelin in the sample for analysis, using analysis means;
   vi) obtaining a concentration of the first compound and/or a ratio between the first compound and sphingomyelin;
   vii) correlating the concentration of vi) with a control value, wherein a concentration equal to or lower than the control value is indicative of the subject having Respiratory Distress Syndrome (RDS); and/or correlating the ratio of vi) with a control ratio, wherein a ratio equal to or lower than the control ratio is indicative of the subject having Respiratory Distress Syndrome (RDS),
   wherein the first and/or the second solution is water or deionized water.

2. The method according to claim 1, wherein the sample has a volume between 10 and 1000 µL.

3. The method according to claim 1, further comprising lysing said cells in said first solution, wherein the first solution is a hypotonic solution.

4. The method according to claim 1, wherein the ratio of the volume of the sample of step i) to the volume of the first solution used in step ii) is between 1:1 and 1:10.

5. The method according to claim 1, wherein the centrifugation of step iii) is performed at a force between 500 and 10000 g for a duration of 1 min to 10 min.

6. The method according to claim 1, wherein the second solution is a hypotonic solution or saline solution.

7. The method according to claim 1, wherein the analysis means is an infrared spectrometer.

8. The method according to claim 1, further comprising determining the amount of a further compound.

9. The method according to claim 1, wherein the time-to-result of the method is between 5 and 60 minutes.

10. The method according to claim 1, wherein the control ratio is between 1.0 and 3.0±0.5.

11. A method of treatment of Respiratory Distress Syndrome (RDS) in a newborn individual, comprising the steps of:
   i) providing a sample from said newborn individual, wherein the sample is an amniotic fluid sample, a blood sample, an oropharyngeal secretion sample or a gastric aspirate sample;
   ii) diluting and homogenising said sample in a first volume of a first solution, thereby obtaining a homogenous sample;
   iii) centrifuging the homogenous sample to obtain a pellet comprising lamellar bodies and a supernatant;
   iv) discarding the supernatant and resuspending the pellet in a second volume of a second solution, thereby obtaining a sample for analysis;
   v) determining the amount of a first compound selected from lecithin and saturated lecithin or determining the amount of a first compound selected from lecithin and saturated lecithin and the amount of sphingomyelin in the sample for analysis, using analysis means;
   vi) obtaining a concentration of the first compound and/or a ratio between the first compound and sphingomyelin;
   vii) correlating the concentration of vi) with a control value, wherein a concentration equal to or lower than the control value is indicative of the subject having Respiratory Distress Syndrome (RDS); and/or correlating the ratio of vi) with a control ratio, wherein a ratio equal to or lower than the control ratio is indicative of the subject having Respiratory Distress Syndrome (RDS); and viii) if the concentration of vi) is equal to or less than the control value and/or if the ratio of vi) is equal to or less than the control ratio, administering a therapeutically effective amount of surfactant to the newborn individual, wherein the first and/or the second solution is water or deionized water.

12. The method according to claim 11, wherein the control ratio is between 1.0 and 3.0±0.5.

13. A system for diagnosing RDS based on a sample obtained from a subject, wherein the sample is an amniotic fluid sample, a blood sample, an oropharyngeal secretion sample or a gastric aspirate sample, and wherein said sample is prepared as per claim 1 wherein said first solution or second solution is water or deionized water, said system comprising a spectroscope for measuring spectral data from said sample, processing means configured for a) determining the activity and/or concentration of a first compound selected from lecithin and saturated lecithin and/or of sphingomyelin in said sample by analysing said spectral data, b) calculating a concentration of the first compound and/or a ratio between the activities and/or concentrations of the first compound and sphingomyelin, and c) correlating said concentration with a control concentration and/or correlating said ratio with a control ratio, and indicating whether the concentration is equal to or lower than the control value and/or indicating if the ratio is equal to or lower than the control ratio, wherein a predefined difference is indicative of Respiratory Distress Syndrome (RDS) of the subject.

14. The method according to claim 1, wherein the control ratio is between 2.0 and 5.0±0.5.

15. The method according to claim 7, wherein the infrared spectrometer is a Fourier transformed infrared (FTIR) spectrometer.

16. The method according to claim 8, wherein the further compound is phosphatidylglycerol.

17. The method according to claim 11, wherein the control ratio is between 2.0 and 5.0±0.5.

* * * * *